(12) United States Patent
Kopren

(10) Patent No.: US 7,740,352 B2
(45) Date of Patent: Jun. 22, 2010

(54) SPORTS VISION TRAINING DEVICE AND METHOD

(76) Inventor: Ted G. Kopren, 433 3rd Ave. NE, Osseo, MN (US) 55369

( * ) Notice: Subject to any disclaimer, the term of this patent is extended or adjusted under 35 U.S.C. 154(b) by 159 days.

(21) Appl. No.: 11/900,171

(22) Filed: Sep. 10, 2007

(65) Prior Publication Data

US 2009/0066907 A1 Mar. 12, 2009

(51) Int. Cl.
*G02C 7/12* (2006.01)
(52) U.S. Cl. .......................................... 351/45; 351/46
(58) Field of Classification Search .................. 351/45, 351/46, 44, 49, 53, 41; 473/210, 268, 227; 33/262, 257, 333, 370–377
See application file for complete search history.

(56) References Cited

U.S. PATENT DOCUMENTS

| | | | |
|---|---|---|---|
| 3,871,104 A * | 3/1975 | Underhill, II | ................ 33/262 |
| 5,177,510 A | 1/1993 | Peters et al. | |
| 5,252,997 A * | 10/1993 | Christenbery | ................ 351/49 |
| 5,521,653 A | 5/1996 | Anderson | |
| 5,675,398 A | 10/1997 | Moore | |
| 5,956,115 A | 9/1999 | Bollé | |
| 6,513,928 B1 | 2/2003 | Moore | |
| 6,558,266 B2 * | 5/2003 | McMahon | ................ 473/210 |
| 6,942,336 B2 | 9/2005 | Foulke et al. | |
| 7,048,371 B1 | 5/2006 | Moore | |
| 7,192,137 B2 | 3/2007 | Ishibashi et al. | |

\* cited by examiner

*Primary Examiner*—Hung X Dang
(74) *Attorney, Agent, or Firm*—Kinney & Lange, P.A.

(57) ABSTRACT

A sports vision training device includes a pair of glasses with a frame supporting a left lens and a right lens. The right lens carries a right reticle, and the left lens carries a left reticle. The reticles provide visual references within the field of view of the player. The reticles may include upper and lower horizontal reference lines, vertical reference lines, a frame, and a crosshair pattern. Different patterns can be used for depth control training, timing control training, and early recognition for tennis and other sports.

10 Claims, 8 Drawing Sheets

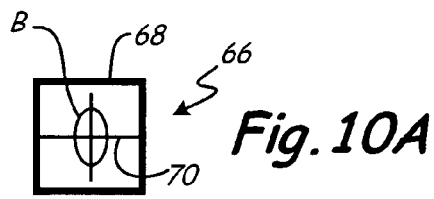
Fig. 10A
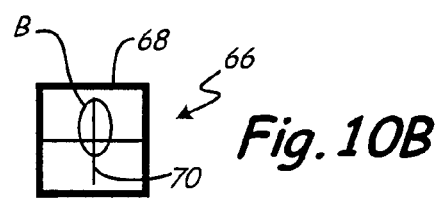
Fig. 10B
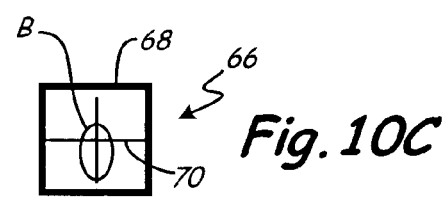
Fig. 10C
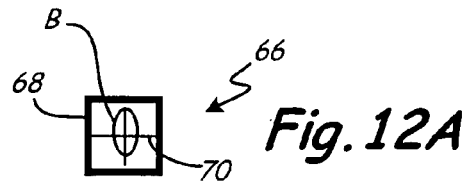
Fig. 12A
Fig. 12B
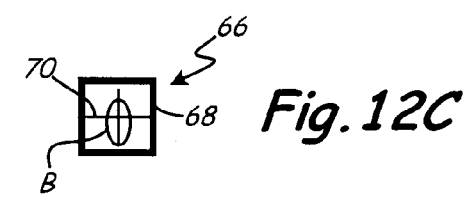
Fig. 12C
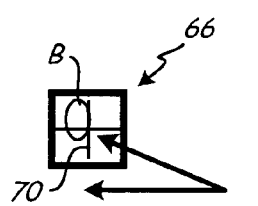
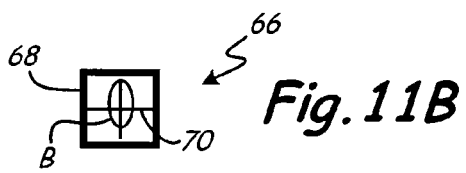
MOVE IMMEDIATELY WITH BALL   Fig. 11A
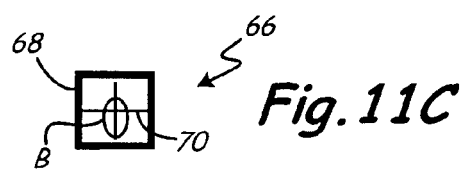
Fig. 11B
Fig. 11C

SPORTS VISION TRAINING DEVICE AND METHOD

BACKGROUND

The present invention relates to sports training, and in particular to sports vision training eyeglasses having lenses that carry reticles to provide visual references within player's field of view.

In many sports, such as tennis and baseball, the ability of the player to obtain proper head positioning while observing a ball during play is extremely important. For example, in tennis proper head positioning can allow a player to see the ball clearly while running, doing a split step, and stroking the ball. Good head positioning leads to better visual processing, balance, consistency, depth control, timing, and overall visual awareness of the ball, the opponent, the court position, and the player during play.

Proper head position allows for maximal use of all visual skills while minimizing extraneous movement of visual-related systems and processing organs. To see a tennis ball traveling at high speed requires positioning the head for minimal eye movement. By keying on an opponent's patterns, early shot recognition, and initial and later head positioning, the amount of head jerking and the angular velocity of the eyes while playing tennis may be minimized, resulting in better tracking of the ball and higher levels of performance.

During a point in a tennis match, there are three phases of observation by a player: shot recognition phase, during which the player watches the opponent hit a shot; tracking phase, during which the player tracks movement of the ball that has been hit by the opponent; and stroking phase, during which the player hits a shot in return. During each of these three phases, the player's head position, focus, and movement into position to hit the ball influence the quality of the player's shot. There are three visual dimensions within each element of each phase: height, width, and depth. Visual errors may occur in any one of the three phases. The main causes of the error have to do with head positioning, visual focus, and body position.

Head positioning is a fundamental element of the dynamic visual process. Proper head positioning reduces visual processing errors, while poor head positioning adds to the problems of dynamic visual processing.

Practice often focuses on motor skills, rather than on the visual skills that guide those motor skills. There is a need for visual training devices that allow athletes to simplify the visual decision process and decrease visual reaction time.

SUMMARY

Improved visual skills can be developed using a sports vision training device in the form of a set of glasses having a frame that supports a left lens and a right lens. At least one lens includes a reticle that provides a reference or references within the player's field of view to aid in reducing the number of other visual cues the brain needs to make decisions, such as the depth, direction, spin, or speed of the ball.

Depending upon the pattern of the reticles, different visual processing skills can be enhanced. For example, sports vision training devices for tennis may include reticles for depth control training, timing control training, and early shot recognition training.

The reticles can be employed by the visual cortex to track and anticipate more accurately and instantly the flight of a ball. The result can be reduced visual reaction response time, more consistent and accurate ball placements, better timing, depth control, balance, improved spatial awareness of the ball, dynamic balance, and instantaneous yet accurate visual feedback for error analysis by the wearer of the sports vision training device.

BRIEF DESCRIPTION OF THE DRAWINGS

FIG. 10A-10C are diagrams that illustrate the use of the early shot recognition vision training device of FIG. 9 for improving visual focus.

FIGS. 11A-11C are diagrams that illustrate the use of the early shot recognition vision training device of FIG. 9 for improving movement to the ball.

FIGS. 12A-12C are diagrams that illustrate the use of the early shot recognition vision training device of FIG. 9 for improving vertical head position.

DETAILED DESCRIPTION

Depth Control Vision Training Device 10

Figure 1:
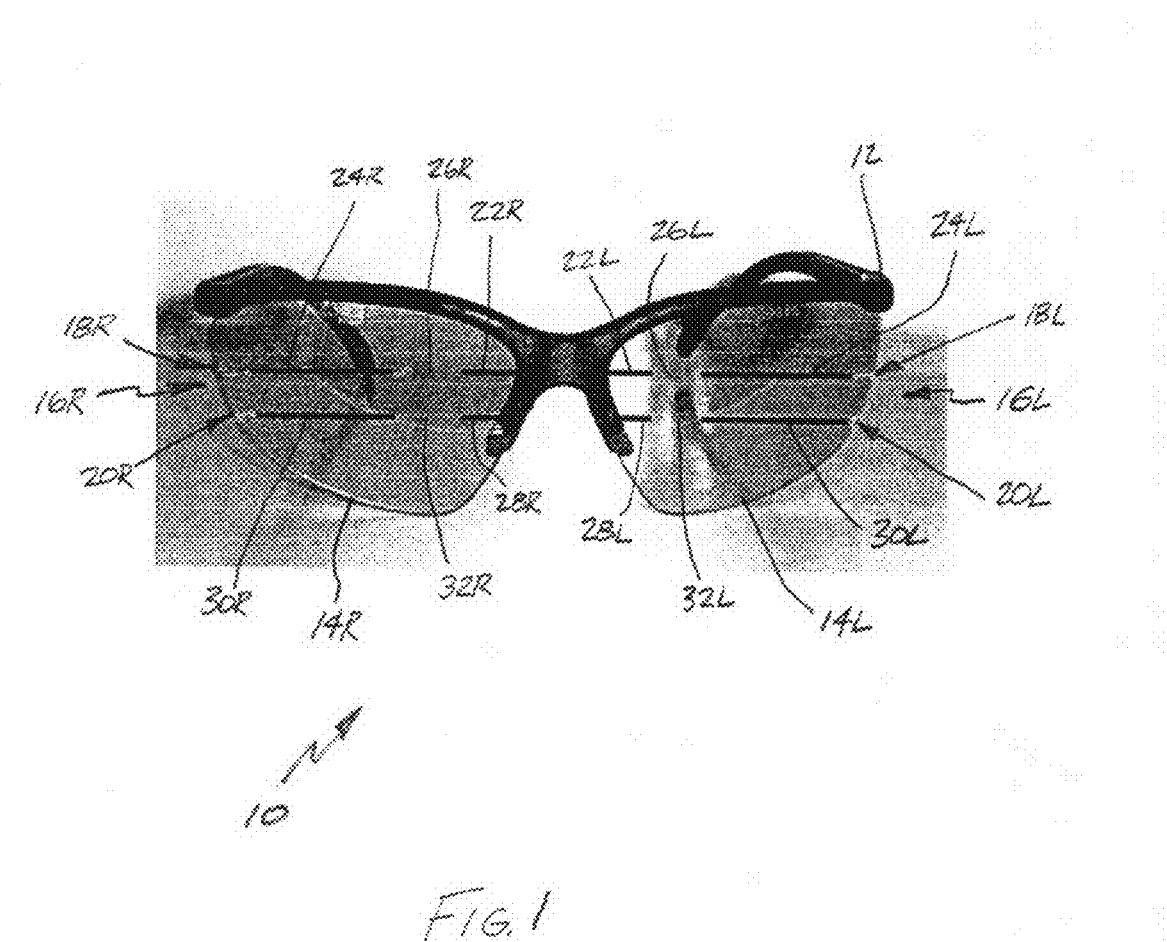
FIG. 1 is a perspective view of a depth control vision training device.

The sports vision training device of the invention makes use of reticles carried by the lenses of a set of glasses to provide visual references that the wearer can use while tracking a ball in play. In the following discussion, three examples of reticles are described for providing depth control, timing control, and early shot recognition training. Other reticles can also be used for these and other vision training programs.

To explain the importance of reticles and how they function during actual play, a description of the design of the visual cortex and its simultaneous interplay with the lens and ball is needed.

The retina, which contains 150,000,000 light sensitive rod and cone cells, is actually an outgrowth of the brain itself. The brain, in trying to effectively handle such a vast array of visual information, uses as many shortcuts as possible. Scientists have found evidence that the brain interprets the brightness of objects based on light-dark contrast, rather than absolute levels of light. The concept of light and dark serves as a basis for making sense of visual information that the brain sorts out and uses to make decisions.

The visual cortex is located in the back of the brain and is about the size of a credit card. The visual cortex has different regions, which are laid out in a logical fashion similar to a road map for a city. This visual "map" helps us determine where we are in relation to whatever we see. Each eye takes in the visual information and transfers it to the visual cortex. When the eyes and vestibular system are functioning well, fusion of the two images from the two eyes occurs. The result, a single clear three dimensional image, is placed in and moves through each of the specific and corresponding regions of the visual cortex to identify where the object is in relation to the person. When both the observer (player) and the object (tennis ball) are moving, dynamic visual processing occurs. As the speed and variety of this process increases, the visual task becomes more challenging. Professional athletes (e.g. tennis players) have developed visual skills specific to their sport (e.g. tennis) to enable them to process visual packets of information quickly and accurately and to make appropriate motor decisions respective to each situation more accurately and consistently than the general population.

Tracking the ball has three dimensions which occur simultaneously from a visual standpoint: the horizontal dimension (width), the vertical dimension (height), and the speed of the ball and the player relative to the ball (depth). With practice, the visual cortex is able to interpret the flight of a tennis ball in each of the three respective dimensions, and then a decision is made where to move to and contact the ball. To help the visual cortex interpret more accurately and quickly where an object is, a reference point or line (i.e. a reticle) can be placed in the visual cortex. This reticle, which is imprinted on the visual cortex by the lens of the training device, is placed in a location and plane so that it acts as a point of reference for more accurately and quickly measuring the trajectory of the oncoming ball. The visual cortex then compares through each sequential "frame" the ball position to the "imprinted" reticle position. The brain can, through the magnified contrast of the imprinted line not previously available, predict with more accuracy the projected flight of the ball, and the player can more quickly and with more precision make an informed visual decision. The placement, width and plane of each line on the lens and where they are imprinted in the visual cortex, in turn affect the decision making ability of the player using the lens.

Without reticles on lenses to provide the position, speed and or arc of the ball, the player must rely on other visual cues which are not typically as clearly distinct and hence somewhat vague as compared to lines on the lens of the glasses. The visual information comes from either the background as a source of comparison, or in a sense the combined experience of the players "visual practice" in a variety of situations. The sheer number of possibilities and vagueness of other reference cues slows the decision process down immensely and increases the resulting reaction time. Through the use of the vision training lenses with reticles, an improved level of performance can be achieved.

FIG. 1 shows depth control vision training device 10, which is a pair of eye glasses including frame 12, left lens 14L and right lens 14R. Lenses 14L and 14R are, typically, non-prescription plastic transparent lenses. Carried on lens 14L is left reticle 16L. Similarly, reticle 16R is carried by right lens 14R.

Reticles 16L and 16R are located within the field of view of the player when wearing training device 10. Left reticle 16L includes upper horizontal reference line 18L and lower horizontal reference line 20L. Similarly, right reticle 16L includes upper horizontal reference line 18R and lower horizontal reference line 20R. Reference lines 18L and 18R are aligned, and lower reference lines 20L and 20R are aligned.

In the embodiment shown in FIG. 1, each of the reference lines 18L, 18R, 20L, and 20R are made up of line segments. Segments 22L and 24L form upper reference line 18L, and define gap 26L between lines 22L and 24L. Similarly, line segments 22R and 24R form upper reference line 18R and define gap 26R.

Line segments 28L and 30L of left lower reference line 20L define gap 32L. Lines 28R and 30R of right lower reference line 20R define gap 32R.

Horizontal lines 18L and 20L on lens 14L, and 18R and 20R on lens 14R are placed, in one embodiment, to provide a visual partition just high enough to view a 4-7 foot high area at 78 feet between the upper and lower horizontal lines.

The position of horizontal reference lines 18L, 18R, 20L and 20R on depth control device 10 are placed just enough to the side of the papillary distance so as to not interfere with the visual field. By the same token, horizontal lines 18L, 18R, 20L, 20R cannot be placed too far vertically above or below the pupils, or tracking effect is lost. Each vision training device is designed to take into account the average pupil positions for men and women. Horizontal lines 18L, 18R, 20L, 20R are then placed above or below the pupils to enable an early contrast of ball flight arc either above or below the net.

Figure 2A:
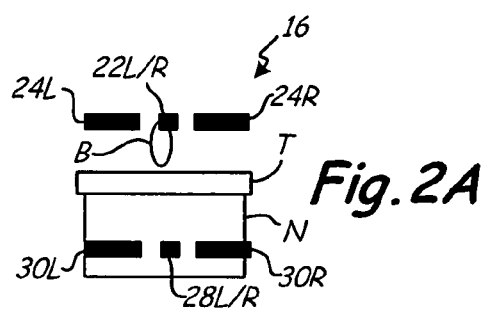
FIGS. 2A-2C are diagrams that illustrate the use of the depth control vision training device of FIG. 1 for improving visual focus.
Figure 2B:
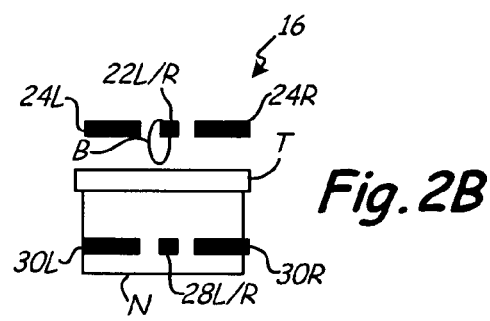
Figure 2C:
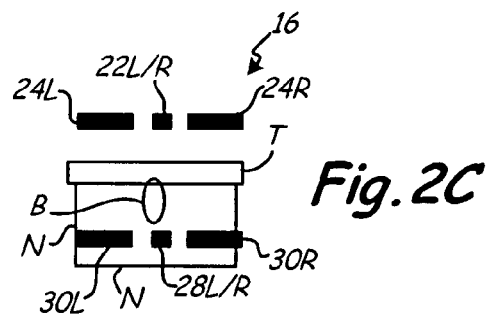

FIGS. 2A-2C illustrate the use of depth control vision training device 10 for improving visual focus. When the player looks through lenses 14R and 14L, and views tennis ball B and tennis net N (and tape T at the top of net N), the images from two eyes of the player are fused to create a single, three-dimensional image. Reticles 16R and 16L merge to form merged reticle 16. The player sees upper horizontal reference line 18 as a composite of lines 18R and 18L, and sees lower horizontal reference line 20 as a composite of lines 20R and 20L.

FIG. 2A shows the image at the time when the opponent strikes the ball. The player has been instructed to line up composite segment 22R/L with ball B at the time of contact. In the image, the player should detect the ball depth, and then immediately move forward or back, as appropriate.

FIG. 2B shows the image as the player is tracking ball B during flight. The player focuses on the bright side of ball B, and notes the arc in the height of ball B. This allows the player to detect top or under spin.

FIG. 2C shows the image when the player has stroked ball B. As ball B bounces, the player focuses on the bright side and notes the height and spin at the time of contact.

Figure 3A:
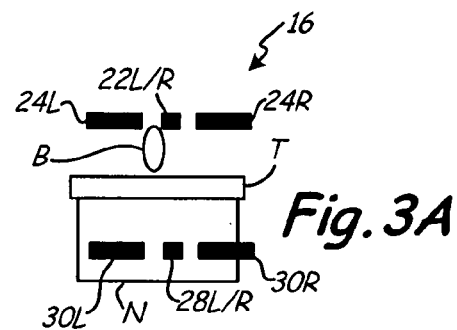
FIGS. 3A-3C are diagrams that illustrate use of the depth control vision training device of FIG. 1 for improving movement to the ball.
Figure 3B:
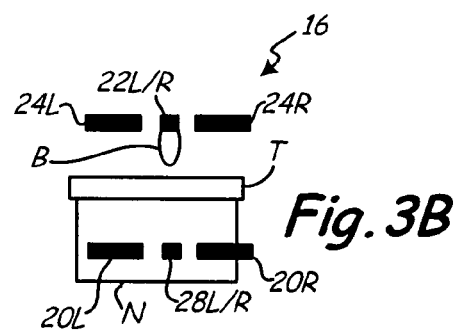
Figure 3C:
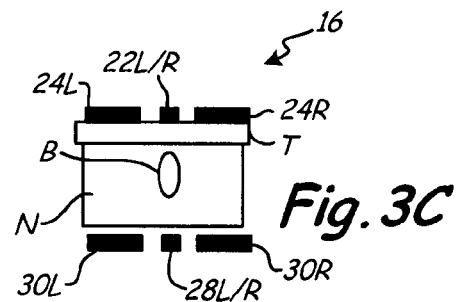

FIGS. 3A-3C show the use of depth control training device 10 to improve movement to the ball. In FIG. 3A, the image is shown at the time when the opponent strikes the ball. The player again detects the ball depth on the lines, and moves immediately forward or back for the ideal contact point.

FIG. 3B shows the image while tracking ball flight. While moving to the ball, the player notes the image and compares the arc with the horizontal line.

FIG. 3C shows the image as the player strokes the ball. As the ball bounces, the player lines up contact the ball so that ball B is centered horizontally and is positioned along the bottom reference line 20.

Figure 4A:
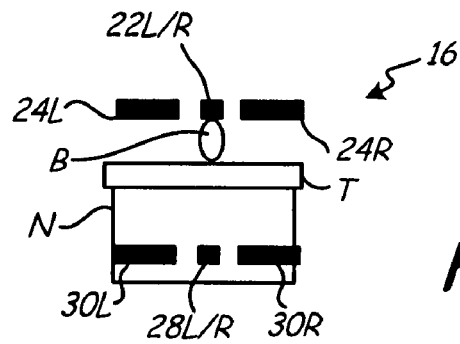
FIGS. 4A-4C are diagrams that illustrate the use of the device of FIG. 1 for improving horizontal head position.
Figure 4B:
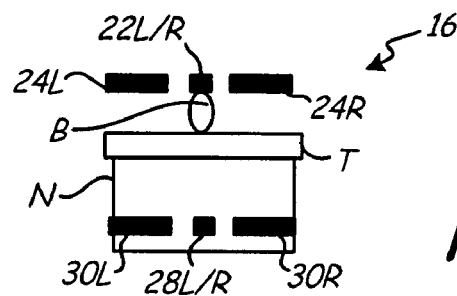
Figure 4C:
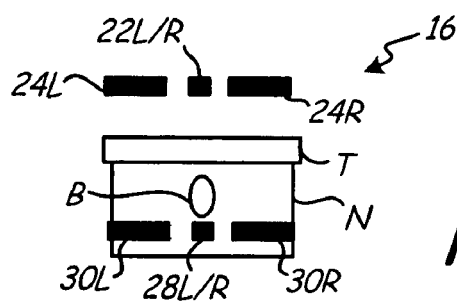

FIGS. 4A-4C show the images created by depth control training device 10. While device 10 is being used to improve horizontal head position.

When the opponent strikes the ball (FIG. 4A, the player positions his/her head so that ball B is aligned with the center segment 22R 22L and 28R 28L. The player focuses on keeping horizontal reference lines 18 and 20 from tipping.

In FIG. 4B, the image is shown as the player is tracking the ball in flight. The player's head position causes the tape T of net N to be between upper and lower horizontal reference lines 18 and 20. The player detects ball depth from this image.

In FIG. 4C, the player strokes the ball. As the ball bounces, the player lines up to contact the ball with net tape T between lines 18 and 20, and then maintains head position after contact so that net tape T remains between reference lines 18 and 20.

The benefits of depth control device 10 include improved consistency of all strokes, improved depth of volleys and strokes, better balance on all strokes, short ball recognition one step earlier, better racquet positioning to the ball at contact, better consistency resulting in increased player confidence, depth recognition of top spin and under spin, and improved shot recognition of top spin serves.

First, early contrast is supplied by each visual frame of processing of the ball flight to horizontal lines 18L, 18R, 20L, 20R. The degree of difference in flight of the ball before a decision can be made is contrasted by the position of lines 18L, 18R, 20L, 20R to the ball. The position of the ball can be compared to the horizontal lines of the reticles imprinted on the visual cortex, as opposed to background which changes and may be less distinct. Visual reaction time is reduced due to simplicity of pattern recognition variables and more accurate contrast in a frame-by-frame process.

Second, during player movement and tracking of the approaching ball, the player can gage the trajectory and depth of the ball more accurately as it approaches. The improved accuracy of the dynamic process of tracking the ball is contrasted with the horizontal lines on the visual cortex as the ball approaches, and sequential player positional adjustments forward or backward can be refined with corresponding accuracy.

Third, during player movement and tracking of the approaching ball with topspin or under-spin (as in a groundstroke or volley), the player can instantly gage the arc or flatness of the ball in a horizontal plane more accurately as it approaches. The improved accuracy of the dynamic process of tracking the ball is contrasted with the horizontal lines on the visual cortex as the ball approaches, and player positional adjustments can be refined with corresponding accuracy.

Fourth, the actual height of the contact point of the shot is improved, either as a volley or after the bounce. Not only is the player able to position himself/herself more precisely to the ball, but also the player will be able to see and contrast with the horizontal lines the ball position and adjust the racquet head height more accurately to provide better contact of shots on the court.

Fifth, the player can also contrast horizontal head position with the net or other visual cues to maintain a horizontal visual field. The player can see instantly the player's head position contrasted with the background before, during and just after contact with the ball. This instant feedback allows the player to compare with the results of the player's shot to determine if the player pulled his/her head up early or if perhaps some other cause may have affected the unplanned ball direction up or down.

Sixth, when fusion does not occur, the ability to maintain a horizontal head position helps maintain the "image" of the ball in the visual cortex in the same up/down plane of the visual field, minimizing miss-hits off the top or bottom of the racquet frame. Consequently, the chance of contacting the sweet spot of the racquet is also increased.

Seventh, because the head of the player is also kept more level and balanced throughout the movement to and during contact with the ball, better depth control results.

Eighth, the contrast sensitivity function is supplanted by providing an additional cue of horizontal lines to contrast with and off the ball.

Timing Control Vision Training Device 40

Figure 5:
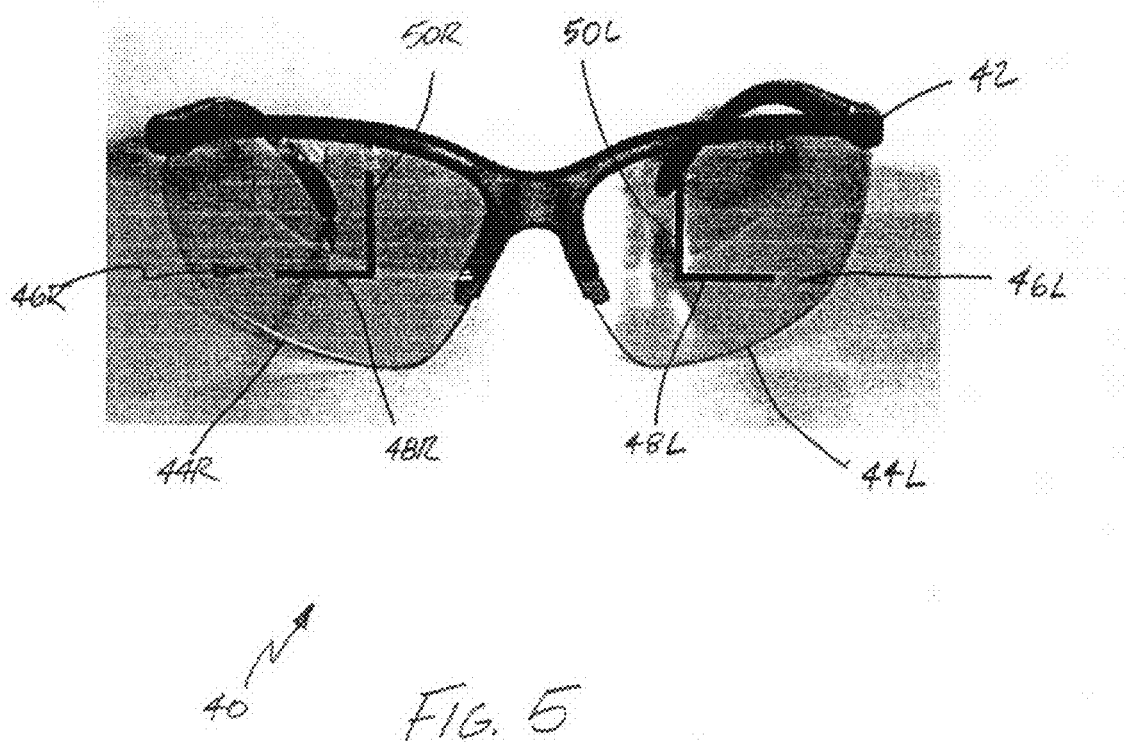
FIG. 5 is a perspective view of a timing control vision training device.

FIG. 5 shows timing control vision training device 40, which includes eye glass frame 42, plastic lenses 44L and 44R, and reticles 46L and 46R. Each reticle 46L, 46R includes a horizontal line 48L, 48R and a vertical line 50L, 50R.

The position of vertical lines 50L, 50R on lenses 44L, 44R is placed just enough to the side of the papillary distance so as to not interfere with the visual field. By the same token vertical lines 50L, 50R cannot be placed too far off to either side of the papillary distance otherwise the effect is negligible. Each timing control device 40 is designed to take into account the average papillary distance for men and women. Vertical line 50L, 50R are placed just laterally by one to three degrees to enable an early contrast of ball flight direction either at, to the right, or left of the player. In one embodiment, vertical lines 50L and 50R are placed on lenses 44L, 44R to provide a visual partition just wide enough to view a 5 foot wide area at 21 feet.

Horizontal lines 48L and 48R provide a horizontal reference for the player. As discussed previously in conjunction with depth control vision training device 10, horizontal reference lines provide feedback to the player on the player's head position.

Figure 6A:
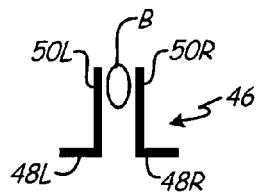
FIGS. 6A-6C are diagrams that illustrate the use of the timing control vision training device of FIG. 5 for improving visual focus.
Figure 6B:
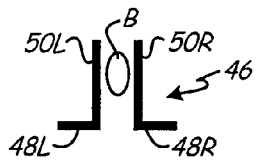
Figure 6C:
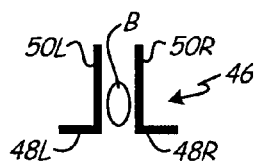

FIGS. 6A-6C shows the use of timing control device 40 for improving visual focus. Fusion of images from the left and right eyes has produced merged reticle 46 in the player's field of view. FIG. 6A shows the image seen by the player when the opponent strikes the ball. The player head positioned his/her head to line up the image of ball B between vertical lines 50L and 50R. The player can detect ball direction using vertical reference lines 50L and 50R, and can move to the left or right as needed.

In FIG. 6B, the image is shown while the player is tracking ball flight. Movement to the ball, the player focuses on the bright side of the ball and maintains ball B between reference lines 50L and 50R.

FIG. 6C shows the image as the player strokes the ball. As the ball bounces, the player focuses on the bright side of the ball. The player maintains vertical head position with the aid of horizontal reference lines 48L and 48R.

Figure 7A:
FIGS. 7A-7C are diagrams that illustrate the use of the timing control vision training device of FIG. 5 for improving movement to the ball.
Figure 7B:
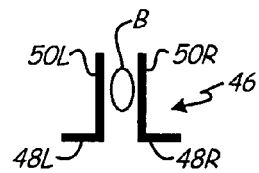
Figure 7C:
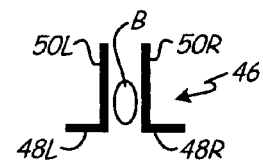

FIGS. 7A-7C illustrates the use of device 40 for improving movement to the ball. When the opponent strokes the ball (FIG. 7A), the player detects ball direction toward vertical lines 50L or 50R, and moves immediately to the left or right with the ball.

FIG. 7B shows the image while tracking the ball flight. During movement to the ball, the player holds the image of ball B between vertical lines 50L and 50R.

In FIG. 7C, the image is shown when the player strokes the ball. As the ball bounces, the player lines up to contact the ball between the line and near the bottom lines 48L and 48R.

Figure 8A:
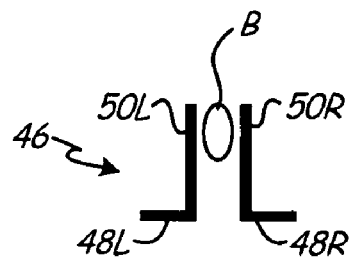
FIGS. 8A-8C are diagrams that illustrate the use of the timing control vision training device of FIG. 5 for improving vertical head position.
Figure 8B:
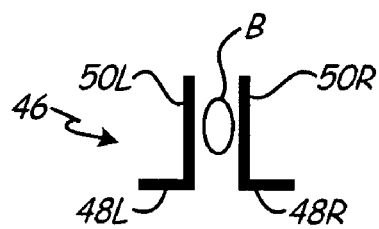
Figure 8C:
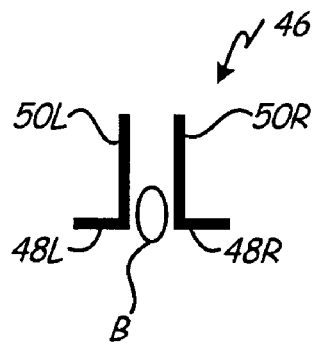

FIGS. 8A-8C show the use of timing control training device 40 for improving vertical head position. In FIG. 8A, the opponent strokes the ball. The player lines up his/her head with the ball between vertical lines 50L 50R at the time of contact and detects ball direction.

In FIG. 8B, the player is tracking ball flight. During movement to the ball, the player holds the ball image between vertical lines 50L and 50R and keeps those lines vertical.

In FIG. 8C, the player strokes the ball. As the ball bounces, the player lines up to contact the ball between lines 50L and 50R and near the bottom lines 48L, 48R. The player uses reticle 46 to maintain vertical head position while stroking the ball.

Timing control vision training device 40 provides a number of benefits. First, early contrast supplied by each visual frame processing the ball flight contrasted to vertical line 50L, 50R, as compared to typical visual information. The degree of difference in flight of the ball before a decision can be made is contrasted by the position of lines 50L, 50R to the ball. By highlighting the ball compared to the vertical lines imprinted on the visual cortex (as opposed to the background which changes), the visual reaction time is reduced due to simplicity of pattern recognition variables and more accurate contrast in a frame-by-frame process.

Second, during player movement and tracking of the approaching ball, the player can gage the trajectory of the ball in a horizontal plane more accurately as it approaches. The improved accuracy of the dynamic process of tracking the ball is contrasted with the vertical line on the visual cortex as the ball approaches, and subsequent player positional adjustments can be refined with corresponding accuracy.

Third, during player movement and tracking of the approaching ball with side spin or slice as in a serve, the player can instantly gage the curve or the ball in a horizontal visual plane more accurately as it approaches. Additionally, the player sees the degree of the curve (slice) of the ball and can move more quickly and accurately along a lateral and vertical plane to the point of contact. The improved accuracy of the dynamic process of tracking the ball is contrasted with the vertical lines on the visual cortex as the ball approaches, and player positional adjustments can be refined with corresponding accuracy.

Fourth, the actual contract point or timing of the shot is improved, either as a volley or a groundstroke after the bounce. Not only is the player positioned more precisely to the ball, but also the player will be able to see and contrast with the vertical lines the ball position, and can time the stroke more accurately to provide better placement of shots on the court.

Fifth, the player can also contrast vertical head position with the net posts or other visual cues to maintain a vertical visual field.

Sixth, when fusion does not occur, the ability to maintain a vertical head position helps maintain the "image" of the ball in the visual cortex in the same right/left plane of the visual field minimizing miss-hits of the throat or end of the frame. Consequently, the chance of contacting the sweet spot of the racquet is also increased.

Seventh, because the head of the player is also kept more stable and balanced throughout the movement to and during contact with the ball, better contact results.

Eighth, the contrast sensitivity function is supplanted by providing an additional cue of vertical lines to contrast with and off the ball to refine the tracking phase.

Early Shot Recognition Vision Training Device 60

Figure 9:
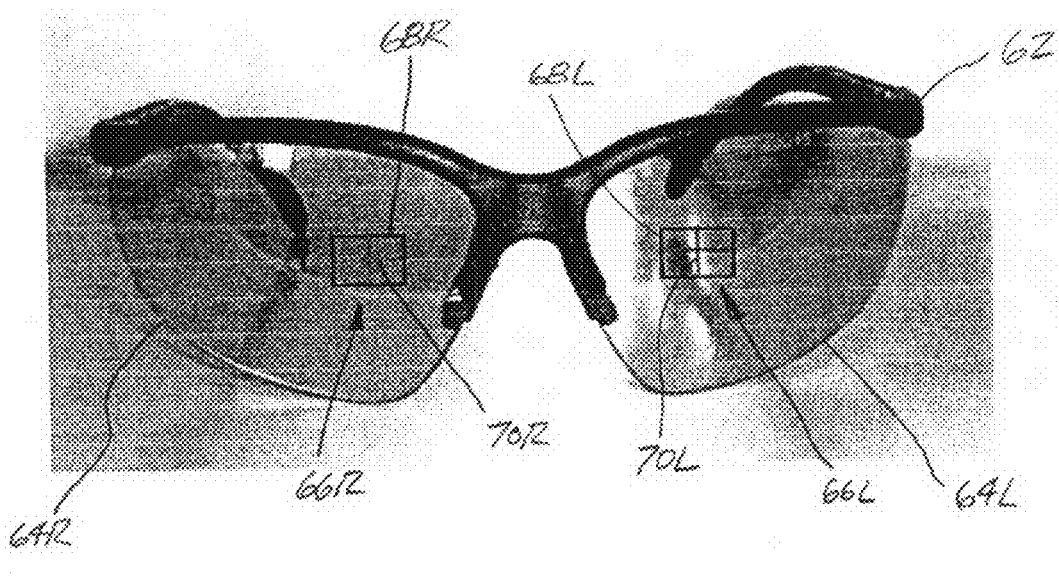
FIG. 9 is a perspective view of early shot recognition vision training device.

FIG. 9 shows early shot recognition vision training device 60, which includes eye glass frame 62, lenses 64L and 64R, and reticles 66L and 66R. Reticle 66L includes a rectangular frame 68L and crosshair pattern 70L. Similarly, reticle 66R includes reticle frame 68R and crosshair pattern 70R. In one embodiment, reticle frames 68L and 68R are black, while crosshair patterns 70L and 70R are red.

Early shot recognition device 60 helps positioning the head of the player to allow for the best visual image to occur by placing the macualae fovea as the center of the visual field during contact with the opponent's stroke. This further refined or more detailed view enhances the early shot recognition process even more so, giving the player "instant" feedback by the degree of quality of the image in the maculae fovea. Instead of a 1 degree differentiation of image there is a 20 minute degree differentiation in quality image of the visual cortex as well. This distinct advantage will improve the anticipation phase by a corresponding differentiation of visual acuity.

Rectangular frames 68L, 68R are used as the framing tool of the image of the opponent and the contact with the ball just as the opponent makes contact with the ball. As illustrated in FIGS. 10A-10C, 11A-11C, and 12A-12C, fusion of images from the right and left eyes produce merged reticle 66 having a box or frame 68 and crosshair pattern 70. The lining up of the head at contact through the small box or frame formed by frames 68L, 68R instantly tells the player whether or not the player's head is lined up to see the opponent's shot. This is the first and most important step in the anticipation stage of visual process of anticipating the shot possible direction and locking in on the ball at contact. The small crosshairs 70 in box 68 serve further as a refinement of the horizontal and vertical lines of devices 10 and 40. Device 60 allows for the ideal position to observe the player hitting the ball and hence a faster visual reaction time. The primary reason that devices 10 and 40 are typically used first in the training process is to begin the appropriate visual progression of learning the tracking of the ball in the vertical and horizontal plane while assisting in maintaining a level head in both planes of ball flight.

FIGS. 10A-10C shows the use of early shot recognition training device 60 for improving visual focus. In FIG. 10A, the opponent strokes the ball. The player views the opponent and the contact point through the visual grid formed by composite frame 68 and composite cross hair 70. The player moves right or left and up and back with the shot.

In FIG. 10B, the player is tracking ball flight. During movement to the ball, the player focuses on the bright side of the ball in frame 68.

In FIG. 10C, the player strokes the ball. As the ball bounces, the player focuses on the bright side of the ball and maintains the vertical head position, so that the ball remains within frame 68.

FIGS. 11A-11C illustrates use of early shot recognition device 60 to improve movement to the ball. In FIG. 11A, the opponent has stroked the ball. The player detects ball motion based upon location of the ball within frame 68 and relative to cross hair 70. Depending upon where the ball is within the quadrant defined by crosshair 70, the player moves immediately with the ball.

FIG. 11B shows tracking of ball flight. During movement to the ball, the player attempts to hold the image of ball B within the center of frame 68, with the aid of cross hair 70.

FIG. 11C shows the image as the player strokes the ball. As the ball bounces, the player lines up to contact the ball, while maintaining balance at contact.

FIGS. 12A-12C shows the use of early shot recognition device 60 for improving vertical head position. In FIG. 12A, the opponent strikes the ball. The player attempts to line up his/her head so that the image of ball B is in the center of frame 68 at the time of contact. The player than detects ball direction based upon the movement of the ball within frame 68.

FIG. 12B illustrates tracking ball flight. During movement to the ball, the player maintains the image of ball B in the center of frame 68. The player also keeps the vertical lines forming frame 68 oriented vertically, so the player is not tipping his/her head.

In FIG. 12C, the player strokes the ball. As the ball bounces, the player lines up to contact the ball and maintains vertical head positioning using frame 68 and cross hair 70 for a reference.

The benefits of early shot recognition device 60 includes the ability to precisely line up at the opponent's contact, improved placement of volley and strokes, reduced visual reaction time making the player one step earlier off to the ball, providing better positioning to the ball at contact, building confidence through better control, providing a best view for the eyes as the opponent hits a shot, and improving shot recognition of all shots.

Although three specific training devices, depth control device 10, timing control device 40, and early shot recognition device 60, have been shown and described, other visual training devices can also make use of the present invention. Different visual skills can be subject to training using reticles of different sizes and shapes. The reticles can be permanently applied to either the front or rear surfaces of the lenses, or may be in the form of detachable overlays that can be applied to the front or rear surfaces of the lenses.

Although the present invention has been described with reference to preferred embodiments, workers skilled in the art will recognize that changes may be made in form and detail without departing from the spirit and scope of the invention.

The invention claimed is:

1. A sports vision training device comprising:
a frame;
a left lens supported by the frame;
a right lens supported by the frame;
a left reticle on the left lens; and
a right reticle on the right lens,
wherein the left and right reticles are placed on the lenses such that the images from the two eyes of the player wearing the device fuse to create a merged reticle for tracking a ball in play and wherein the left and right reticles each include an upper horizontal reference line and a lower horizontal reference line wherein at least one of the upper and lower horizontal lines includes line segments separated by a space.

2. The device of claim 1, wherein each of the upper and lower horizontal lines includes line segments separated by a space.

3. A sports vision training device comprising:
a frame;
a left lens supported by the frame;
a right lens supported by the frame;
a left reticle on the left lens;
a right reticle on the right lens,
wherein the left and right reticles are placed on the lenses such that the images from the two eyes of the player wearing the device fuse to create a merged reticle for tracking a ball in play, wherein the left and right reticles each include a vertical reference line, wherein the left and right reticles each further include a horizontal reference line, and wherein the horizontal reference line is connected to and extends outward from one end of the vertical reference line.

4. The device of claim 3, wherein each of the horizontal reference lines is connected to and extends outward from the bottom ends of the vertical reference lines.

5. A sports vision training device comprising:
a frame;
a left lens supported by the frame;
a right lens supported by the frame;
a left reticle on the left lens; and
a right reticle on the right lens,
wherein the left and right reticles are placed on the lenses such that the images from the two eyes of the player wearing the device fuse to create a merged reticle for tracking a ball in play, and wherein the left and right reticles each include a reticle frame.

6. The device of claim 5, wherein the left and right reticles each further include a crosshair pattern within the reticle frame.

7. The device of claim 5, wherein the reticle frame comprises a rectangle.

8. A sports vision training device comprising:
a frame;
a pair of lenses supported by the frame; and
a reticle on at least one of the pair of lenses,
wherein the reticle comprises a vertical reference line and a horizontal reference line,
wherein the horizontal reference line is connected to and extends outward from the lower end of the vertical reference line,
wherein the reticle is positioned on the lens such that when the device is worn, the reticle provides a reference to aid in maintaining a steady head position and in tracking the flight of a ball in motion.

9. A sports vision training device comprising:
a frame;
a pair of lenses supported by the frame; and
a reticle on at least one of the pair of lenses,
wherein the reticle comprises a closed frame,
wherein the reticle is positioned on the lens such that when the device is worn, the reticle provides a reference to aid in maintaining a steady head position and in tracking the flight of a ball in motion.

10. A sports vision training device comprising:
a frame;
a pair of lenses supported by the frame; and
a reticle on at least one of the pair of lenses,
wherein the reticle comprises a crosshair pattern enclosed in a frame,
wherein the reticle is positioned on the lens such that when the device is worn, the reticle provides a reference to aid in maintaining a steady head position and in tracking the flight of a ball in motion.

* * * * *